US011071301B2

(12) United States Patent
Li et al.

(10) Patent No.: US 11,071,301 B2
(45) Date of Patent: Jul. 27, 2021

(54) ANTI-MICROBIAL AGENT TO CONTROL BIOMASS ACCUMULATION IN SO2 SCRUBBERS

(71) Applicant: ECOLAB USA INC., Saint Paul, MN (US)

(72) Inventors: Junzhong Li, Saint Paul, MN (US); Chris Nagel, Saint Paul, MN (US); Laura Rice, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 269 days.

(21) Appl. No.: 15/783,169

(22) Filed: Oct. 13, 2017

(65) Prior Publication Data

US 2018/0110224 A1    Apr. 26, 2018

Related U.S. Application Data

(60) Provisional application No. 62/411,233, filed on Oct. 21, 2016.

(51) Int. Cl.
| | | |
|---|---|---|
| *A01N 43/88* | (2006.01) | |
| *A01N 33/12* | (2006.01) | |
| *A01N 35/02* | (2006.01) | |
| *A01N 41/10* | (2006.01) | |
| *A01N 47/40* | (2006.01) | |
| *B01D 53/50* | (2006.01) | |
| *C02F 1/50* | (2006.01) | |
| *A61L 2/18* | (2006.01) | |
| *A01N 47/48* | (2006.01) | |
| *A01N 47/14* | (2006.01) | |
| *C02F 103/18* | (2006.01) | |
| *B01D 53/77* | (2006.01) | |

(52) U.S. Cl.
CPC ............ *A01N 43/88* (2013.01); *A01N 33/12* (2013.01); *A01N 35/02* (2013.01); *A01N 41/10* (2013.01); *A01N 47/14* (2013.01); *A01N 47/40* (2013.01); *A01N 47/48* (2013.01); *A61L 2/18* (2013.01); *C02F 1/50* (2013.01); *A61L 2202/14* (2013.01); *A61L 2202/20* (2013.01); *A61L 2202/24* (2013.01); *B01D 53/50* (2013.01); *B01D 53/77* (2013.01); *C02F 2103/18* (2013.01)

(58) Field of Classification Search
CPC ........ A01N 43/88; A01N 47/14; A01N 47/48; A01N 47/40; A01N 41/10; A01N 35/02; A01N 33/12; A61L 2/18; A61L 2202/20; A61L 2202/14; A61L 2202/24; C02F 1/50; C02F 2103/18; B01D 53/77; B01D 53/50

See application file for complete search history.

(56) References Cited

U.S. PATENT DOCUMENTS

| | | | |
|---|---|---|---|
| 2,917,428 A | 12/1959 | Hitzman | |
| 4,088,743 A * | 5/1978 | Hass | B01D 53/52 423/539 |
| 4,802,994 A | 2/1989 | Mouché et al. | |
| 4,802,996 A | 2/1989 | Mouchè et al. | |
| 5,206,151 A | 4/1993 | Robertson | |
| 5,374,536 A | 12/1994 | Robertson | |
| 5,494,588 A | 2/1996 | LaZonby et al. | |
| 5,658,467 A | 8/1997 | LaZonby et al. | |
| 5,922,745 A | 7/1999 | McCarthy et al. | |
| 6,096,225 A | 8/2000 | Yang et al. | |
| 6,254,801 B1 | 7/2001 | Reinold et al. | |
| 6,267,897 B1 * | 7/2001 | Robertson | C02F 5/10 210/764 |
| 6,440,689 B1 | 8/2002 | Banks et al. | |
| 6,576,629 B1 | 6/2003 | Oppong et al. | |
| 6,840,251 B2 | 1/2005 | Gill et al. | |
| 7,772,156 B2 | 8/2010 | Bryant | |
| 2002/0114856 A1 | 8/2002 | Cooper et al. | |
| 2005/0150520 A1* | 7/2005 | Gill | A61L 2/18 134/22.1 |
| 2009/0242484 A1 | 10/2009 | Urmenyi et al. | |
| 2011/0028525 A1 | 2/2011 | Diehl et al. | |
| 2011/0052453 A1* | 3/2011 | McLarnon | B01D 53/501 422/170 |
| 2011/0217728 A1 | 9/2011 | Yin | |
| 2012/0087827 A1 | 4/2012 | Temple | |
| 2013/0190214 A1 | 7/2013 | Kolari et al. | |
| 2013/0225456 A1 | 8/2013 | Figueredo | |
| 2014/0003995 A1 | 1/2014 | Temple | |

(Continued)

FOREIGN PATENT DOCUMENTS

| | | |
|---|---|---|
| CA | 803486 A | 7/1969 |
| CA | 2131664 A1 | 3/1995 |

(Continued)

OTHER PUBLICATIONS

Frayne, The Analyst, pp. 1-14 (Year: 2001).*
Liberatore, Lolita et al., "Chemical and Biological Combined Treatments for the Removal of Pesticides from Wastewaters", Water, Air, & Soil Pollution, pp. 4751-4759, vol. 223, Issue 8, published online Jun. 16, 2012.
Brozel, V.S. et al., "Resistance of Bacterial Cultures to Non-Oxidising Water Treatment Bactericides by Adaptation", Water Science and Technology, pp. 169-175, vol. 31, Issues 5-6 available online 1995.

(Continued)

*Primary Examiner* — Abigail Vanhorn
(74) *Attorney, Agent, or Firm* — McKee, Voorhees & Sease, PLC (57) ABSTRACT

A method for removing or preventing a microbial growth, biofilm, biomass and/or mineral deposit on a hard surface inside an $SO_2$ scrubber is disclosed. In particular, biocide compositions may be dosed in pulse or continuously for the reduction and prevention of biofilms on the hard surfaces inside an $SO_2$ scrubber. A biocide composition disclosed here uses one or more non-oxidizing biocides, especially a mixture of one or more quaternary ammonium compounds and one or more other biocides.

20 Claims, 1 Drawing Sheet

(56) References Cited

U.S. PATENT DOCUMENTS

| | | |
|---|---|---|
| 2014/0202206 A1 | 7/2014 | Temple et al. |
| 2014/0271757 A1 | 9/2014 | Agrawal et al. |
| 2014/0303045 A1 | 10/2014 | Campbell et al. |
| 2015/0351383 A1 | 12/2015 | Kolari et al. |
| 2015/0351389 A1 | 12/2015 | Kolari et al. |
| 2016/0227769 A1 | 8/2016 | Gandhi et al. |

FOREIGN PATENT DOCUMENTS

| | | | |
|---|---|---|---|
| CA | 2300807 A1 | 9/2000 | |
| CN | 101244856 A | 8/2008 | |
| CN | 104542584 A | 4/2015 | |
| EP | EP-0261607 A2 * | 3/1988 | ............... C02F 1/50 |
| EP | 0774444 A1 | 5/1997 | |
| WO | 9420424 A1 | 9/1994 | |
| WO | 199934013 A1 | 7/1999 | |
| WO | 2007070609 A2 | 6/2007 | |
| WO | 2011006019 A2 | 1/2011 | |
| WO | 2012113042 A1 | 8/2012 | |
| WO | 2016196115 A1 | 12/2016 | |

OTHER PUBLICATIONS

Van Leeuwen, C.J. et al., "Aquatic Toxicological Aspects of Dithiocarbamates and Related Compounds. I. Short-Term Toxicity Tests", Aquatic Toxicology, pp. 145-164, vol. 7, Issue 3 Jul. 26, 1985.

Ecolab Use Inc., PCT/US2017/056485 filed Oct. 13, 2017, "Notification of Transmittal of the International Search Report and the Written Opinion of the International Searching Authority, or the Declaration", dated Nov. 27, 2017.

\* cited by examiner

ANTI-MICROBIAL AGENT TO CONTROL BIOMASS ACCUMULATION IN SO2 SCRUBBERS

CROSS-REFERENCE TO RELATED APPLICATIONS

This application claims priority under 35 U.S.C. § 119 to provisional application U.S. Ser. No. 62/411,233, filed Oct. 21, 2016, which is herein incorporated by reference in its entirety.

FIELD OF THE INVENTION

The invention relates to use of non-oxidizing anti-microbial agents for removal of biofilm growth and other impurities and prevention of microbial growth, biomass and/or mineral deposit on a hard surface inside a $SO_2$ scrubber. Accordingly, the present invention relates to the field of biofilm control of $SO_2$ scrubbers. In particular, several chemical compounds, optionally in combination with quaternary ammonium compound(s) can be provided in a biocide composition for the reduction, prevention, removal and/or kill of biofilms and the mitigation of other impurities on such hard surfaces. The compositions according to the invention beneficially provide biofilm control, therefore reducing or eliminating the use of the existing cleaning method, which requires stopping scrubbers' normal operation and causes $SO_2$ vapor leakage into environment.

BACKGROUND OF THE INVENTION

Industrial processing surfaces, including scrubbers, are conventionally treated using clean-in-place (CIP) methods to provide flushing, rinsing, pretreatment, cleaning, disinfecting, sanitizing and preserving, in order to prevent fouling during processing. Fouling components and deposits can include inorganic salts, particulates, microbials and organics. Fouling manifests itself as a decline in performance and increased energy consumption, and/or quality of the finished goods. Fouling can also include biofilm growth along with other impurities within industrial processing systems, such as $SO_2$ scrubbers employed in grain oil, biofuels, and other specialty chemicals, having detrimental results. As a result, CIP processes are utilized to circulate cleaning agents over and through the industrial processing surfaces to wet, penetrate, dissolve and/or rinse away foreign materials. Various parameters that can be manipulated for cleaning typically include time, temperature, mechanical energy, chemical composition, chemical concentration, soil type, water type, and hydraulic design. Conventional cleaning techniques include the use of high heat and/or extreme pH, i.e., very high alkalinity use solutions, or very low pH acidic use solutions. However, many surfaces cannot tolerate such conditions.

In an exemplary large corn wet milling operation, $SO_2$ is emitted from variety of process equipment where corn or other grains or seeds is processed and tower $SO_2$ scrubbers are used to remove $SO_2$ gas. In $SO_2$ scrubbers, $SO_2$ and air mixture is usually pumped in from the bottom of the scrubbers with a blower. As $SO_2$ arises, it encounters an alkaline agent, gets fixed in solution, and converts to mainly sulfite salt. As in many conventional applications to increase $SO_2$ contact with the alkaline agent, $SO_2$ scrubbers employ plastic balls or other packing materials to lengthen and alter $SO_2$ path. Since the environment for this $SO_2$ fixation process is substantially anaerobic, alkaline, and warm (usually around or at least about 90° F.), it is ideal for microbial growth to form biofilms.

Biofilms are biological conglomerates that contain pathogens, such as bacteria and other microorganisms, embedded in a matrix of exopolymers and macromolecules. In addition to bacteria, other microorganisms are commonly found in biofilm, including fungi, molds, algae, protozoa, archaea and mixtures of these microorganisms. Biofilms form as a result of microorganisms establishing on a surface and producing a protective extracellular polymeric matrix. Most often biofilms form on surfaces in contact with water, providing a hydrated matrix of polysaccharides to provide structural protection from biocides, making biofilm more difficult to kill than other pathogens.

Microbial infection and the formation of biofilm present significant complications in numerous industries. Although biofilm is known to exist in a wide-variety of environmental conditions, and biofilms most often form on surfaces exposed to bacteria and water, industries such as paper making and food and grain processing are particularly affected by biofilms. These applications can occur in various aspects of the processing systems, including for example within papermaking, fiber prepared to make paper, sheets/boards prepared for water removal phase, and water removal phases where biofilms present a significant challenge. For example, the organism *Listeria monocytogenes* thrives in cool, damp environments, such as floor drains, plumbing and other surfaces of food processing facilities. This provides a potential point of contamination for a processing plant environment and food products produced therein. Exposure to such microorganisms may result in infections and compromise the public's health. Therefore, controlling the formation of biofilm is desirable to decrease exposure to infectious microorganisms.

Inside $SO_2$ scrubbers, biofilms form inside the scrubbers and the surfaces of the packing materials, causing plugging, fouling, reduction of optimal flow, including air flow, and potential contamination of the plant environments.

Biofilm growth and removal depends on several factors, including the surface composition and chemical composition of the surrounding environment. Several biofilm removal methods are utilized, including physical, chemical and biological removal. Means of physically removing biofilm include the use of magnetic fields, ultra sound, high and low electrical fields and abrasive techniques. Physical removal techniques are often combined with chemical or biological methods, such as biocides or antimicrobial agents. A number of technologies have been developed that treat surfaces with organic or inorganic materials to interfere with biofilm development, such as preventing microbial attack and promoting biofilm degradation. For example, coating a surface with or incorporating a composition into a surface substrate to create a surface wherein microorganisms do not adhere or colonize. U.S. Pat. No. 9,072,292. However, such technologies have not effectively eliminated biofilm formation and growth. Therefore, the contamination of surfaces with biofilm remains a problem.

Among various biocides known, peroxycarboxylic acids are increasingly used as antimicrobials and bleaching agents in many applications, owing to their high efficacy against a broad spectrum of microorganisms, color safe property, low residues and nontoxic nature of their decomposition products. However, for $SO_2$ scrubbers, oxidizers such as peracids cannot be used without the disruption of the process due to the reducing nature of $SO_2$ and the sodium sulfite formed. As a result, use of conventional oxidizers such as peracids would result in the oxidizers being consumed by the $SO_2$ and the sodium sulfite formed, and as a result no beneficial antimicrobial effects and control of biofilm would take place, or such large quantities of the oxidizers would be required to overcome the reducing environment of the $SO_2$ scrubbers that such methods would be cost prohibitive and expose the systems to substantial amounts of chemistry. The common current practice for $SO_2$ scrubber cleaning is using large amount of bleach to remove the formed biofilms and kill other microorganisms. This cleaning process needs to be done usually once a week with a lot of bleach while the normal scrubber operation is stopped. It is expensive and also allows some $SO_2$ to escape into the environment.

In light of the foregoing, there remains a demand for compositions and methods for removing and inhibiting biofilm inside $SO_2$ scrubbers. Furthermore, although various agents preventing microbial growth, such as oxidizers and biocides, are known for cleaning industrial processing surfaces, including CIP cleaning techniques, there is still a need for an improved method for the prevention of microbial growth and biofilm formation inside $SO_2$ scrubbers.

Accordingly, it is an objective of the claimed invention to provide a method using non-oxidizing biocides for the prevention and removal of microbial growth and biofouling from industrial processing surfaces, including those inside $SO_2$ scrubbers.

Other objects, advantages and features of the present invention will become apparent from the following specification taken in conjunction with the accompanying examples or drawings.

BRIEF SUMMARY OF THE INVENTION

The invention provides a method using a biocide or non-oxidizing biocide composition to remove and/or inhibit microbial or biofilm growth from industrial processing surfaces, including $SO_2$ scrubbers. Examples of contaminants include, for example, particulate matter, organic and inorganic contaminants, oils, process contaminants, microorganisms, and so forth. Suspended matter in the industrial processes, and waters associated therewith, provide the microorganisms with readily available nourishment for sustaining life and reproduction. It is well established that the presence of inorganic, organic, and microbiological deposits have a detrimental impact on the operational parameters of an industrial processing system, resulting in reduced efficiency and increased operating cost.

In an aspect, methods of the invention are directed to methods of removing or preventing microbial/biofilm growth, biomass, other impurities, and/or mineral deposit on a hard surface inside industrial $SO_2$ scrubbers. In a further aspect, the methods of the invention are directed to intermittent treatment of aqueous solutions used in industrial $SO_2$ scrubber's operation with the non-oxidizing biocide compositions. Beneficially, the non-oxidizing biocide compositions provide effective microbial/biofilm growth, biomass, other impurities, and/or mineral deposit and removal thereof, while without stopping the normal operation of the scrubbers and reducing the frequency of the scrubber's stoppage for cleaning purposes.

In an aspect, a method for removing and/or preventing microbial growth and biofilm on a hard surface inside an $SO_2$ scrubber system comprises: contacting a hard surface inside an $SO_2$ scrubber system with a biocide composition comprising from about 0.1 ppm to 300 ppm one or more biocides, wherein the biocide comprises 3,5-dimethyl-tetrahydro-2H-1,3,5-thiadiazine-2-thione, sodium dimethyldithiocarbamate, disodium ethylene bis-dithiocarbamate, bis-(trichloromethyl)-sulfone, glutaraldehyde, or combinations thereof, wherein the biocide composition removes or prevents microbial growth and biofilm on the surface.

In a further aspect, a method for removing and/or preventing microbial growth and biofilm on a hard surface inside an $SO_2$ scrubber system comprises: contacting a hard surface inside an $SO_2$ scrubber system with a biocide composition comprising from about 0.1 ppm to 300 ppm one or more biocides, wherein the biocide comprises a quaternary ammonium compound and at least one of 3,5-dimethyl-tetrahydro-2H-1,3,5-thiadiazine-2-thione, sodium dimethyldithiocarbamate, disodium ethylene bis-dithiocarbamate, bis-(trichloromethyl)-sulfone, glutaraldehyde, or combinations thereof, wherein the biocide composition removes or prevents microbial growth and biofilm on the surface.

In an aspect, methods of the invention are directed to methods of cleaning surfaces in industrial $SO_2$ scrubbers between conventional clean-in-place (CIP) cleaning methods or to replace them. In a further aspect, methods of the invention are directed to methods of preventing microbial or biofilm growth on surfaces in industrial $SO_2$ scrubbers, to reduce and/or eliminate the CIP cleaning of such surfaces.

In a further embodiment, the present invention discloses the non-oxidizing biocide compositions comprising one or more non-oxidizing biocides that efficiently kill and remove, or prevent biofilms and other soils, contaminants and impurities formation without damaging or negatively interfering with the treated surfaces.

In a further embodiment, the present invention discloses the non-oxidizing biocide compositions comprising one or more quaternary ammonium compounds and one or more non-oxidizing other biocides to remove or prevent microbial or biofilm growth and other contaminants and impurities deposit.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to biocide or non-oxidizing biocide compositions comprising one or more biocides, for use to reduce and/or prevent biofilm growth and other contaminants and impurities from treated surfaces inside an $SO_2$ scrubber. The embodiments of this invention are not limited to any particular biocide compositions, which can vary and are understood by skilled artisans based on the disclosure herein of the present invention. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, a sulfone is referred to a compound represented by a formula, wherein $R^{10}$ and $R^{11}$ are independently a substituted or substituted alkyl group. An exemplary sulfone is bis(trichloromethyl)-sulfone.

As used herein, a dithiocarbamate derivative is referred to a compound containing a group or salt thereof, wherein the R12 is a substituted or substituted alkyl group.

As used herein, a thiocyanate derivative is referred to a compound containing a group.

As used herein, a tetrahydro-2H-1,3,5-thiadiazine-2-thione derivative is referred to a compound represented by a formula wherein $R^{13}$ and $R^{14}$ are independently a substituted or substituted alkyl group.

According to an aspect of the invention, a non-oxidizing biocide composition may comprise a quaternary ammonium compound. Quaternary ammonium compounds are those of the general formula I:

which may also be depicted according to the following general formula II:

wherein $R^1$, $R^2$, $R^3$ and $R^4$ (formula 1; or R, R', R", R''' respectively for formula 2) independently of each other represent alkyl groups, aliphatic groups, aromatic groups, alkoxy groups, polyoxyalkylene groups, alkylamido groups, hydroxyalkyl groups, aryl groups, $H^+$ ions, each with from 1 to 22 carbon atoms, with the provision that at least one of the groups $R^1$, $R^2$, $R^3$ and $R^4$ has at least eight carbon atoms and wherein X(–) represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms. Additional description of quaternary ammonium groups is set forth, for example, in U.S. Pat. No. 8,221,733, which is herein incorporated by reference in its entirety. Suitable quaternary ammonium containing groups are often referred to as quaternary ammonium compound or quaternary ammonium cation compound, which are still further commonly referred to as a "quat." Exemplary quaternary ammonium compounds include, for example, alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof.

Exemplary alkylated quaternary ammonium compounds include ammonium compounds having an alkyl group containing between C6-C24. Exemplary alkylated quaternary ammonium compounds include monoalkyl trimethyl quaternary ammonium compounds, monomethyl trialkyl quaternary ammonium compounds, and dialkyl dimethyl quaternary ammonium compounds. The alkyl group can be a C8-C22 group or a C8-C18 group or a C12-C22 group that is aliphatic and saturated or unsaturated or straight or branched, an alkyl group, a benzyl group, an alkyl ether propyl group, hydrogenated-tallow group, coco group, stearyl group, palmityl group, and soya group. Further, exemplary ring or cyclic quaternary ammonium compounds include imidazolinium quaternary ammonium compounds, such as methyl-1hydr. tallow amido ethyl-2-hydr. tallow imidazolinium-methyl sulfate, methyl-1-tallow amido ethyl-2-tallow imidazolinium-methyl sulfate, methyl-1-oleyl amido ethyl-2-oleyl imidazolinium-methyl sulfate, and 1-ethylene bis(2-tallow, 1-methyl, imidazolinium-methyl sulfate).

Additional suitable cationic active ingredients include triamines having the general formula:

wherein $R^1$ is an alkyl group, in some aspects a C6-C18 alkyl group. Alkyl includes unbranched or branched alkyl groups of the specified number of carbons, but preferably unbranched alkyl groups, and particularly preferably those having an even number of carbon atoms.

Additional exemplary quaternary ammonium compounds include alkanolamines, which include all ethanolamines and propanolamines, in particular monoethanolamine, diethanolamine, triethanolamine and 3-amino-1-propanol. Alkanolamines have the following general structure:

wherein where n and, if present, m and o independently of one another have the value 2 or 3, and x and y independently of one another have the value 0 or 1, or a corresponding salt. In an aspect, employing mixtures of the alkanolamines is also within the scope of embodiments of the invention.

Still further, exemplary aromatic quaternary ammonium compounds include those compounds that have at least one benzene ring in the structure. Exemplary aromatic quaternary ammonium compounds include dimethyl alkyl benzyl quaternary ammonium compounds, monomethyl dialkyl benzyl quaternary ammonium compounds, trimethyl benzyl quaternary ammonium compounds, and trialkyl benzyl quaternary ammonium compounds. Further, the alkyl group can contain between about 6 and about 24 carbon atoms, and can contain between about 10 and about 18 carbon atoms, and can be a stearyl group or a hydrogenated tallow group. Aromatic quaternary ammonium compounds can include multiple benzyl groups. Exemplary alkoxylated quaternary ammonium compounds include methyldialkoxy alkyl quaternary ammonium compounds, trialkoxy alkyl quaternary ammonium compounds, trialkoxy methyl quaternary ammonium compounds, dimethyl alkoxy alkyl quaternary ammonium compounds, and trimethyl alkoxy quaternary ammonium compounds. The alkyl group can contain between about C6-C24 and the alkoxy groups can contain between about 1 and about 50 alkoxy groups units wherein each alkoxy unit contains between about C2-C3. Exemplary amidoamine quaternary ammonium compounds may include methyl-bis(tallow amidoethyl)-2-hydroxyethyl ammonium methyl sulfate, methyl bis(oleylamidoethyl)-2-hydroxyethyl ammonium methyl sulfate, and methyl bis(hydrtallowamidoethyl)-2-hydroxyethyl ammonium methyl sulfate.

Some quaternary ammonium compounds that can be used in the biocide compositions according to the invention include, for example, but are not limited to, alkyl dimethyl benzyl ammonium chloride, alkyl dimethyl ethyl benzyl ammonium chloride, dialkyl dimethyl ammonium chloride, octyl decyl dimethyl ammonium chloride, dioctyl dimethyl ammonium chloride, didecyl dimethyl ammonium chloride, benzethonium chloride, N, N-bis-(3-aminopropyl) dodecylamine, chlorhexidine gluconate, an organic and/or organic salt of chlorhexidene gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

The term "biofilm," as used herein, means an extracellular matrix in which a population of microorganisms are dispersed and/or form colonies. Biofilms are understood to be typically made of polysaccharides and other macromolecules, often referred to as exopolysaccharides, that are concentrated at an interface (usually solid/liquid) and act as a binding agent that surrounds such populations of microorganisms. Biofilms are further understood to include complex associations of cells, extracellular products and detritus (or non-living particulate organic material) that are trapped within the biofilm or released from cells within the biofilm. The term biofilm, as used herein, further refers to the ASTM definition of biofilm as an accumulation of bacterial cells immobilized on a substratum and embedded in an organic polymer matrix of microbial origin. Biofilms are understood to be a dynamic, self-organized accumulation of microorganisms and microbial and environmental by-products that is determined by the environment in which it lives. According to the invention, the phrases "biofilm remediation," "removing biofilm," "reducing biofilm" and like phrases, shall mean the use of the chemical biocide according to the invention which causes a reduction in the rate or extent of biofilm growth, removal of existing biofilm or portions of biofilm on surfaces and/or eradication of existing biofilm on a treated surface. According to the invention, the biocidal compositions disclosed herein physically remove and kill biofilm.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As it pertains to this disclosure, "fouling" and "contamination" refer to the presence or the deposition of any extraneous or undesirable organic or inorganic material in a water-containing industrial process or onto one or more surfaces within the water-containing industrial process. "Microbial fouling" refers to the presence or deposition of any extraneous or undesirable microbiological organism in a water-containing industrial process.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces. A hard surface also refers to a surface of a pipe, tower, container, or equipment that has contact with chemicals used in $SO_2$ scrubber's operation. Additional surfaces in a scrubber may include pipes, pumps, valves, distribution plates, sumps, packing materials, tower surfaces, demisters, stage plates etc.

As used herein, the terms "mixed" or "mixture" when used relating to "non-oxidizing biocide composition", "biocides", or "biocide composition" refer to a composition or mixture including more than one biocide. As used herein, the terms "microbiocide" and "biocide" are used interchangeably and are meant to include chemicals used to control "pests" as defined under the Federal Insecticides Fungicide and Rodenticide Act (FIFRA) in both aqueous and non-aqueous fluid systems.

The term biocide is clearly defined in the art as any type of antimicrobial agent that is capable of producing kill in biological systems. The term biocide is also used in the art to refer to antimicrobial agents (a subset of biocides) that are inhibitory, and are agents that prevent biological growth or biological systems from actively metabolizing. The antimicrobial agent is defined as containing one or a blend of one or more biocides. In general, an antimicrobial agent is microcidal or microstatic, although microcidal can also refer to biocidal, meaning "cidal" (killing) against biologic systems or microbiocidal, meaning "cidal" against microbial systems, a subgroup of biological systems. These terms are used interchangeably in industry and are understood to be interchangeable by one familiar with the art.

As used herein, a biocide is usually referred to a biocidal active substance, instead of a biocidal product, biocide composition, or biocide product. The biocidal active substances or biocides are mostly chemical compounds as used herein. Biocide composition or biocide products contain one or more biocidal active substances and may contain other non-active co-formulants that ensure the effectiveness as well as the desired pH, viscosity, color, odor, etc. of the final product.

Biocides are commonly used in medicine, agriculture, forestry, and industry. Biocidal substances and products are also employed as anti-fouling agents or disinfectants under other circumstances. However, a biocide composition has not been used in $SO_2$ scrubber's operation.

For the purpose of this patent application, successful microbial reduction is achieved when the microbial populations are reduced by at least about 50%, or by significantly more than is achieved by a wash with water. Larger reductions in microbial population provide greater levels of protection.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage.

The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both.

As used herein, the term "waters" includes cooling tower waters. Cooling tower waters include water being used in scrubbers, cooling towers and the like, including where water is performing the function of collecting impurities, capturing product and/or cooling the equipment.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The methods and non-oxidizing biocide compositions according to the embodiments of the invention present a significant improvement in the prior art and represent a significant change for industries in need of cleaning $SO_2$ scrubbers. The antimicrobial and biofilm remediation methods and compositions according to the invention obviate the need for numerous antimicrobial and biofilm-reducing agents that are individually and/or in combination unable to completely remove and/or kill biofilm. The antimicrobial and biofilm remediation compositions according to the invention provide a superior antimicrobial and biocidal product, resulting in improved kill rates of microbes and biofilm over existing methods of chemical and biological removal or reduction. This is a beneficial result of the antimicrobial and biofilm remediation compositions according to the invention having a "kill mechanism" capable of penetrating all layers of an antimicrobial and biofilm composition and reaching the substrate surface. These and other benefits of the antimicrobial and biofilm remediation methods and compositions according to the invention will be readily apparent based on the description contained here, providing improved compositions and methods for treating ubiquitous biofilm inside $SO_2$ scrubbers.

Various antimicrobial and biofilm-reducing agents are known to provide some beneficial effects in biofilm reduction and/or prevention. For example, chelating agents such as EDTA and EGTA, chlorine, iodine and hydrogen peroxide have previously been used as biofilm-reducing agents. Chelating agents destabilize the outer cell membrane of the biofilm. Chlorine, iodine, and hydrogen peroxide remove biofilm by depolymerizing the matrix. Further, antimicrobial and biofilm-reducing agents may include antimicrobial proteins, such as nisin, which may be produced by *Lactococcus lactus*. Biocides or antimicrobial agents are also used as biofilm-reducing agents. Examples of biocides or antimicrobial agents that are effective include: iodophores; phenols including halo- and nitrophenols and substituted bisphenols such as 4-hexylresorcinol, 2-benzyl-4-chlorophenol and 2,4, 4'-trichloro-2'-hydroxydiphenyl ether; quaternary ammonium compounds and other cationic compounds; cationic surfactants such as alkyl and benzyl quaternary compounds like N-alkyl ($C_{12}$-$C_{18}$) dimethylbenzyl ammonium chloride monohydrate, dimethyl didecyl ammonium chloride, and N-alkyl and ($C_{12}$-$C_{14}$) dimethyl I-napthylmethyl ammonium chloride; organic and inorganic acids and its esters and salts such as dehydroacetic acid, methyl p-hydroxy benzoic acid; aldehydes such as glutaraldehyde; antimicrobial dyes such as is acridines, triphenylmethane dyes and quinones and halogens.

However, as described according to the invention, some other biocides or a combination of two or more biocides and methods described herein provide enhanced antimicrobial "-cidal" mechanisms that are superior over prior biofilm-reducing agents used in cleaning $SO_2$ scrubbers. For example, according to a preferred embodiment, a biocide composition comprising a combination of one or more non-oxidizing biocides and optionally one or more quaternary ammonium compounds provides effective reduction in the population of microorganisms and pathogens in biofilm, even in a very low concentration, without generating any foams.

Methods of Cleaning Industrial Processing Surfaces in $SO_2$ Scrubbers

The present invention comprises a non-oxidizing biocide composition which can be used to remove or inhibit biofilm growth and formation from $SO_2$ scrubbers. As referred to herein, the removing of microorganisms, biofilm, contaminants and other impurities refers to the reduction in microorganisms, biofilm, contaminants and other impurities from a hard surface within an industrial $SO_2$ scrubber system, the disbursement of microorganisms, biofilm, contaminants and other impurities from such surfaces, and/or the inactivating of microorganisms, biofilm, contaminants and other impurities from such surfaces.

In an aspect, the non-oxidizing biocide compositions are applied to or contact a hard surface in an $SO_2$ scrubber system, in need of removing/inhibiting microbial growth and biofilm.

Figure 1:
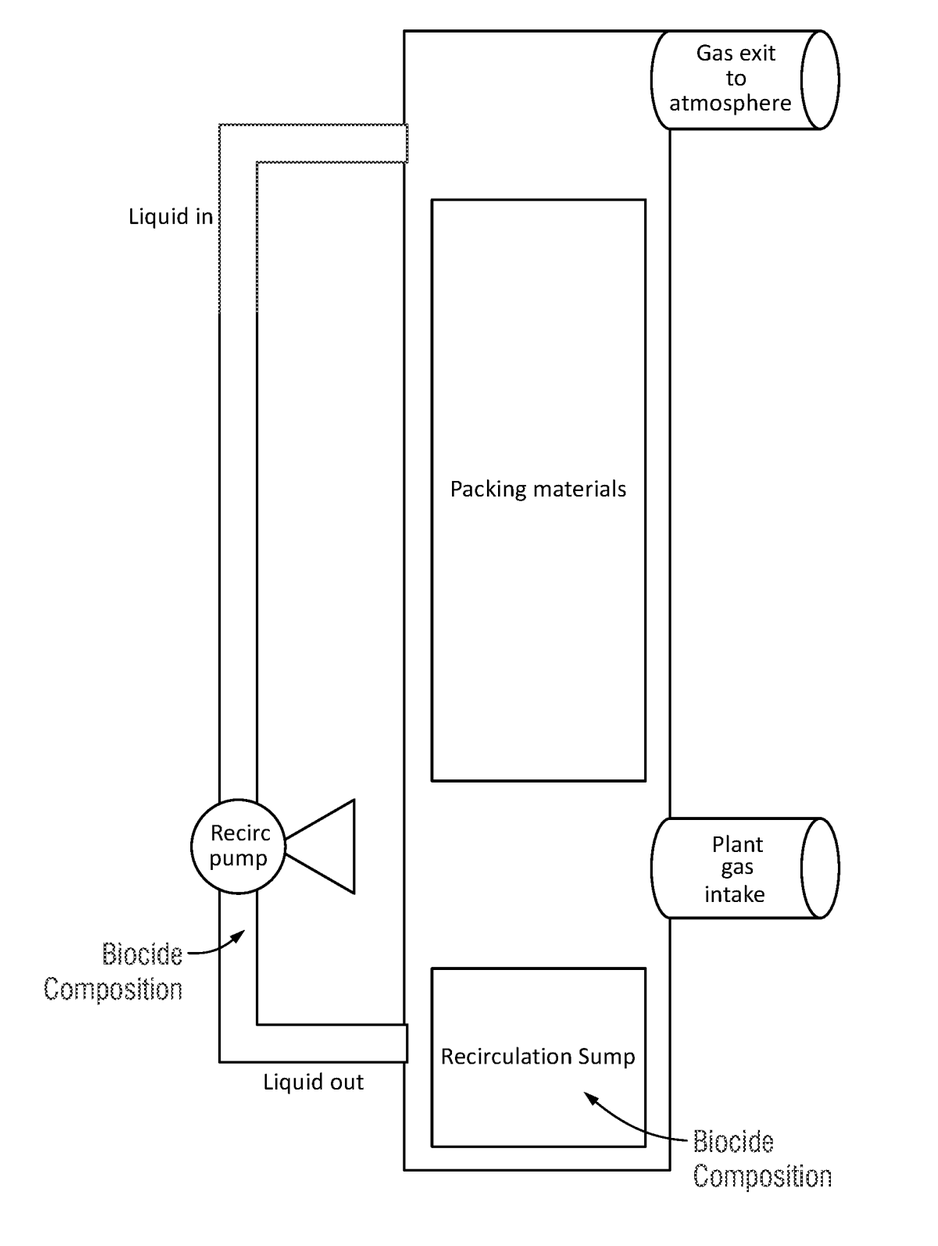
The FIGURE shows an overview diagram of an embodiment of the methods wherein a biocide composition can be added to a system containing an $SO_2$ scrubber.

In a non-limiting exemplary embodiment, The FIGURE shows an overview diagram of an $SO_2$ scrubber that could be contained and/or utilized in various systems. In such a depicted embodiment, a biocide and/or biocide composition can be added into a sump (or a recirculation sump) and/or at a recirculation pump of a system to provide the biocide and/or biocide composition into the $SO_2$ scrubber to remove and/or inhibit microbial growth and biofilm. Beneficially, the biocide and/or biocide composition is circulated through the $SO_2$ scrubber in the system, including contacting the hard surfaces therein. The hard surfaces that can be treated according to the invention include any surfaces for a pipe, equipment, or towers that have contact with the gases and liquids used in the $SO_2$ scrubber's operations. Additional surfaces in a scrubber may include pipes, pumps, valves, packing materials, tower surfaces, distribution plates, sumps, demisters, stage plates etc. In an aspect, hard surfaces that can be treated according to the invention include any hard surface with a water and/or air interface with packing materials employed in the $SO_2$ scrubber's operations. These can include for example, the metallic, plastic and/or other materials which can be provided in the form of spherical balls to increase surface area of gas for $SO_2$.

The methods of treating an industrial processing surface with the biocide compositions can include a plurality of steps. A first step can be referred to as a product removal step or displacement where product (e.g. contaminants and impurities such as aldehydes and alcohols, etc.) is removed from the industrial processing system. In some aspects, such product can be effectively recovered and used as opposed to discharging as plant effluent. The product removal step can last as long as it takes to remove and recover product from the industrial $SO_2$ scrubbing processing system. In general, it is expected that the product removal step will take at least a couple minutes for most systems.

In a preferred aspect, an on-site and/or in-line generator feeds the biocide composition to an industrial processing system. In an aspect, the biocide is fed or dosed into an aqueous solution that is regularly used in $SO_2$ scrubber's normal operation, on a periodic basis or continuously. In an exemplary embodiment, the one or more biocides are fed into an aqueous solution for about 30 minutes about every 4 hours to form a desired biocide concentration in the aqueous solution, turning the aqueous solution into a biocide composition. In an aspect, a biocide composition of from about 0.1 to about 300 ppm biocide(s), or from about 0.1 to about 150 ppm biocide(s) is formed in the processing system, or from about 5 to about 15 ppm biocide(s), or still further from about 50 to about 150 ppm biocide(s). Without limiting the scope of the methods and compositions described herein, all numeric ranges recited are inclusive of the numbers within the defined range.

In an aspect of the invention, a controller or programmable device provides scheduled dosing and control of other onsite and/or in-line dosing and delivery of water and/or other biocide actives to the system. In such an aspect, a controller is capable of shutting off other chemical feeds at the time of dosing the biocide(s) or creating the biocide composition. In an embodiment, the biocide(s) can be dosed into the water feed line of the scrubber, turning the feed water into the biocide composition and treating the scrubber.

In an exemplary dosing interval, the biocide composition is dosed on an interval suitable to prevent the growth of microbes and the formation of any biofilm. As referred to herein, the interval refers to the amount of time between the dosing of the biocide composition. In an exemplary embodiment, a dosing interval to provide the biocide composition is at least once a week. In a further embodiment, a dosing interval to provide the biocide composition is at least once every other day. In a further embodiment, a dosing interval to provide the biocide composition is at least once a day. In a further embodiment, a dosing interval to provide the biocide composition is at least about every 12 hours, 11 hours, 10 hours, 9 hours, 8 hours, 7 hours, 6 hours, 5 hours, 4 hours, 3 hours, 2 hours, 1 hour or less than an hourly basis. In a still further embodiment, dosing can be provided in a constant dose. In a preferred exemplary embodiment, a dosing interval for the biocide composition is particularly suitable to prevent the growth of microbes and the formation of any biofilm, including at an interval of from about 2 to about 10 hours between dosing, or about 3 to about 5-hour interval. Without being limited to a particular mechanism of action according to the present invention, in an exemplary embodiment, a 4-hour dosing interval is suitable based upon the doubling time of most microbes, preventing a biofilm to get a foothold on a surface. In such an embodiment, after about 30 minutes of biocide acid treatment, the controller shuts off the dosing and/or generating of the biocide(s).

In a preferred aspect, the dosing of the biocide compositions does not require a plant or facility to shut down or stop the $SO_2$ scrubbers for the dosing of the biocide composition. This beneficially overcomes a significant limitation of the conventional means of cleaning, which employ large amounts of bleach or other oxidizing chemistries. In an aspect, the $SO_2$ scrubbers can be run continuously and dosed the biocide composition without shutting down or suspending operation thereof.

In one aspect, the present invention provides a method for removing or preventing microbial growth and biofilm on a hard surface inside an $SO_2$ scrubber, the method comprises contacting a hard surface inside an $SO_2$ scrubber with a biocide composition comprising from about 0.1 ppm to 300 ppm one or more non-oxidizing biocides, wherein the one or more biocides are dosed continuously or in pulse into the biocide composition, and the biocide composition removes or prevents a microbial growth, biomass and/or mineral deposit caused by a microorganism from the surface.

In some embodiments, the one or more biocides are dosed in a liquid solution used in $SO_2$ scrubber normal operation.

In some embodiments, the one or more biocides can be dosed together in combination or can be dosed sequentially.

In some embodiments, the one or more biocides are selected from the group consisting of a tetrahydro-2H-1,3,5-thiadiazine-2-thione derivative (also referred to as thione), sulfone, dithiocarbamate derivative, thiocyanate derivative, quaternary ammonium compound, and a combination thereof.

In some other embodiments, the one or more biocides are selected from the group consisting of 3,5-dimethyl-tetrahydro-2H-1,3,5-thiadiazine-2-thione, tetrahydro-2H-1,3,5-thiadiazine-2-thione derivative, methylene bisthiocyanate, thiocyanate derivative, 1-$C_{16}$-$C_{18}$-alkylamino-3-aminopropane acetate, bis(trichloromethyl) sulfone, sulfone, 5-chloro-2-methyl-4-isothiazolin-3-one, 2-methyl-4-isothiazolin-3-one, quaternary ammonium compound, 2,2-dibromo-3-nitrilo-propionamide (DBNPA), 2-(thiocyanomethylthio)-benzothiazole, sodium dimethyldithiocarbamate, disodium ethylene bis-dithiocarbamate, dithiocarbamate, glutaraldehyde, 1-(3-chloroallyl)-3,5,7-triazoniaadamatane, chloride N-4-dihydroxy-alpha oxobenzene chloride, sodium hypochlorite 4,5-dichloro-1,2-dithio-3-one, n-dodecylguanidine hydrochloride, decythioethylamine and combination thereof.

In some embodiments, the one or more biocides are 3,5-dimethyl-tetrahydro-2H-1,3,5-thiadiazine-2-thione, sodium dimethyldithiocarbamate, disodium ethylene bis-dithiocarbamate, bis-(trichloromethyl)-sulfone, glutaraldehyde, quaternary ammonium compound, or a combination thereof.

In some other embodiments, the one or more biocides are one or more quaternary ammonium compounds and one or more of 3,5-dimethyl-tetrahydro-2H-1,3,5-thiadiazine-2-thione, tetrahydro-2H-1,3,5-thiadiazine-2-thione derivative, methylene bisthiocyanate, 1-$C_{16}$-$C_{18}$-alkylamino-3-aminopropane acetate, bis(trichloromethyl) sulfone, 5-chloro-2-methyl-4-isothiazolin-3-one, 2-methyl-4-isothiazolin-3-one, quaternary ammonium compound, 2,2-dibromo-3-nitrilo-propionamide (DBNPA), 2-(thiocyanomethylthio)-benzothiazole, sodium dimethyldithiocarbamate, disodium ethylene bis-dithiocarbamate, dithiocarbamate, glutaraldehyde, 1-(3-chloroallyl)-3,5,7-triazoniaadamatane, chloride N-4-dihydroxy-alpha oxobenzene chloride, sodium hypochlorite 4,5-dichloro-1,2-dithio-3-one, n-dodecylguanidine hydrochloride, and decythioethylamine.

In some embodiments, the biocide composition comprises from about 0.1 ppm to about 300 ppm, from about 0.1 ppm to about 250 ppm, from about 0.1 ppm to about 200 ppm, from about 0.1 ppm to about 150 ppm, from about 0.5 ppm to about 150 ppm, from about 1 ppm to about 150 ppm, from about 5 ppm to about 150 ppm, from about 10 ppm to about 150 ppm, from about 15 ppm to about 150 ppm, from about 20 ppm to about 150 ppm, from about 25 ppm to about 150 ppm, from about 30 ppm to about 150 ppm, from about 35 ppm to about 150 ppm, from about 40 ppm to about 150 ppm, from about 45 ppm to about 150 ppm, from about 50 ppm to about 150 ppm, from about 55 ppm to about 150 ppm, from about 60 ppm to about 150 ppm, from about 65 ppm to about 150 ppm, from about 70 ppm to about 150 ppm, from about 75 ppm to about 150 ppm, from about 80 ppm to about 150 ppm, from about 85 ppm to about 150 ppm, from about 90 ppm to about 150 ppm, from about 95 ppm to about 150 ppm, from about 100 ppm to about 150 ppm, from about 110 ppm to about 150 ppm, from about 120 ppm to about 150 ppm, from about 130 ppm to about 150 ppm, from about 140 ppm to about 150 ppm, from about 0.1 ppm to about 1 ppm, from about 1 ppm to about 10 ppm, from about 10 ppm to about 20 ppm, from about 20 ppm to about 30 ppm, from about 30 ppm to about 40 ppm, from about 40 ppm to about 50 ppm, from about 50 ppm to about 60 ppm, about 60 ppm to about 70 ppm, from about 70 ppm to about 80 ppm, from about 80 ppm to about 90 ppm, from about 90 ppm to about 100 ppm, from about 100 ppm to about 110 ppm, from about 110 ppm to about 120 ppm, from about 120 ppm to about 130 ppm, from about 130 ppm to about 140 ppm, or from about 140 ppm to about 150 ppm the one or more biocides.

In some other embodiments, the biocide composition comprises from about 0.1 ppm to about 300 ppm, from about 0.1 ppm to about 250 ppm, from about 0.1 ppm to about 200 ppm, from about 0.1 ppm to about 150 ppm, from about 0.1 ppm to about 140 ppm, from about 0.1 ppm to about 130 ppm, from about 0.1 ppm to about 120 ppm, from about 0.1 ppm to about 110 ppm, from about 0.1 ppm to about 100 ppm, from about 0.1 ppm to about 90 ppm, from about 0.1 ppm to about 80 ppm, from about 0.1 ppm to about 70 ppm, from about 0.1 ppm to about 60 ppm, from about 0.1 ppm to about 50 ppm, from about 0.1 ppm to about 40 ppm, from about 0.1 ppm to about 30 ppm, from about 0.1 ppm to about 20 ppm, from about 0.1 ppm to about 10 ppm, from about 0.1 ppm to about 1 ppm, from about 0.5 ppm to about 150 ppm, from about 0.5 ppm to about 140 ppm, from about 0.5 ppm to about 130 ppm, from about 0.5 ppm to about 120 ppm, from about 0.5 ppm to about 110 ppm, from about 0.5 ppm to about 100 ppm, from about 0.5 ppm to about 90 ppm, from about 0.5 ppm to about 80 ppm, from about 0.5 ppm to about 70 ppm, from about 0.5 ppm to about 60 ppm, from about 0.5 ppm to about 50 ppm, from about 0.5 ppm to about 40 ppm, from about 0.5 ppm to about 30 ppm, from about 0.5 ppm to about 20 ppm, from about 0.5 ppm to about 10 ppm, from about 0.5 ppm to about 5 ppm, from about 1 ppm to about 150 ppm, from about 1 ppm to about 140 ppm, from about 1 ppm to about 130 ppm, from about 1 ppm to about 120 ppm, from about 1 ppm to about 110 ppm, from about 1 ppm to about 100 ppm, from about 1 ppm to about 90 ppm, from about 1 ppm to about 80 ppm, from about 1 ppm to about 70 ppm, from about 1 ppm to about 60 ppm, from about 1 ppm to about 50 ppm, from about 1 ppm to about 40 ppm, from about 1 ppm to about 30 ppm, from about 1 ppm to about 20 ppm, or from about 1 ppm to about 10 ppm one or more biocides.

In some other embodiments, the biocide composition comprises from about 10 ppm to about 300 ppm, from about 10 ppm to about 250 ppm, from about 10 ppm to about 200 ppm, from about 10 ppm to about 150 ppm, from about 10 ppm to about 140 ppm, from about 10 ppm to about 130 ppm, from about 10 ppm to about 120 ppm, from about 10 ppm to about 110 ppm, from about 10 ppm to about 100 ppm, from about 10 ppm to about 90 ppm, from about 10 ppm to about 80 ppm, from about 10 ppm to about 70 ppm, from about 10 ppm to about 60 ppm, from about 10 ppm to about 50 ppm, from about 10 ppm to about 40 ppm, from about 10 ppm to about 30 ppm, from about 10 ppm to about 20 ppm, from about 20 ppm to about 150 ppm, from about 20 ppm to about 140 ppm, from about 20 ppm to about 130 ppm, from about 20 ppm to about 120 ppm, from about 20 ppm to about 110 ppm, from about 20 ppm to about 100 ppm, from about 20 ppm to about 90 ppm, from about 20 ppm to about 80 ppm, from about 20 ppm to about 70 ppm, from about 20 ppm to about 60 ppm, from about 20 ppm to about 50 ppm, from about 20 ppm to about 40 ppm, from about 20 ppm to about 30 ppm, from about 30 ppm to about 140 ppm, from about 30 ppm to about 130 ppm, from about 30 ppm to about 120 ppm, from about 30 ppm to about 110 ppm, from about 30 ppm to about 100 ppm, from about 30 ppm to about 90 ppm, from about 30 ppm to about 80 ppm, from about 30 ppm to about 70 ppm, from about 30 ppm to about 60 ppm, from about 30 ppm to about 50 ppm, or from about 30 ppm to about 40 ppm one or more biocides.

In some other embodiments, the biocide composition comprises from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 50 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.5 ppm to about 100 ppm, from about 0.5 ppm to about 200 ppm, from about 0.5 ppm to about 300 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 1 ppm to about 100 ppm, from about 1 ppm to about 200 ppm, from about 1 ppm to about 300 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and glutaraldehyde.

In still some other embodiments, the biocide composition comprises from about 1 ppm to about 15 ppm, from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and a sulfone.

In some other embodiments, the biocide composition comprises from about 10 ppm to about 100 ppm, from about 10 ppm to about 200 ppm, from about 10 ppm to about 300 ppm, from about 10 ppm to about 150 ppm, from about 20 ppm to about 150 ppm, from about 30 ppm to about 150 ppm, from about 50 to about 150 ppm, from about 100 ppm to about 150 ppm, from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 50 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and dithiocarbamate, or one or more dithiocarbamates.

In some other embodiments, the biocide composition comprises from about 1 ppm to about 25 ppm from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and thiocyanate derivative.

In some other embodiments, the biocide composition comprises from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and tetrahydro-2H-1,3,5-thiadiazine-2-thione derivative.

In some other embodiments, the biocide composition comprises from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and bis-(trichloromethyl) sulfone.

In some other embodiments, the biocide composition comprises from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds, disodium ethylene bis-dithiocarbamate, and dimethyldithiocarbamate.

In some embodiments, the biocide composition comprises from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and methylenebisthiocyanate.

In some other embodiments, the biocide composition comprises from about 0.1 ppm to about 1 ppm, from about 0.1 ppm to about 10 ppm, from about 0.1 ppm to about 15 ppm, from about 0.1 ppm to about 15 ppm, about 0.1 ppm to about 25 ppm, from about 0.1 ppm to about 30 ppm, from about 0.1 ppm to about 35 ppm, from about 0.1 ppm to about 40 ppm, from about 0.1 ppm to about 45 ppm, from about 0.1 ppm to about 50 ppm, from about 0.1 ppm to about 100 ppm, from about 0.1 ppm to about 200 ppm, from about 0.1 ppm to about 300 ppm, from about 0.5 ppm to about 1 ppm, from about 0.5 ppm to about 10 ppm, from about 0.5 ppm to about 15 ppm, from about 0.5 ppm to about 15 ppm, about 0.5 ppm to about 25 ppm, from about 0.5 ppm to about 30 ppm, from about 0.5 ppm to about 35 ppm, from about 0.5 ppm to about 40 ppm, from about 0.5 ppm to about 45 ppm, from about 0.5 ppm to about 50 ppm, from about 0.1 ppm to about 1 ppm, from about 0.1 ppm to about 10 ppm, from about 1 ppm to about 15 ppm, from about 1 ppm to about 15 ppm, about 1 ppm to about 25 ppm, from about 1 ppm to about 30 ppm, from about 1 ppm to about 35 ppm, from about 1 ppm to about 40 ppm, from about 1 ppm to about 45 ppm, from about 1 ppm to about 50 ppm, from about 10 ppm to about 15 ppm, from about 10 ppm to about 25 ppm, from about 10 ppm to about 30 ppm, from about 10 ppm to about 35 ppm, from about 10 ppm to about 40 ppm, from about 10 ppm to about 45 ppm, from about 10 ppm to about 50 ppm, from about 20 ppm to about 50 ppm, about 20 ppm to about 25 ppm, from about 20 ppm to about 30 ppm, from about 20 ppm to about 35 ppm, from about 20 ppm to about 40 ppm, from about 20 ppm to about 45 ppm, from about 20 ppm to about 50 ppm, from about 30 ppm to about 50 ppm, from about 40 ppm to about 45 ppm, or from about 40 ppm to about 50 ppm one or more quaternary ammonium compounds and 3,5-dimethyl-tetrahydro-2H-1,3,5-thiadiazine-2-thione.

In some embodiments, the biocide composition has a pH of about 7, about 8, about 9, about 10, about 11, about 12, from about 7 to about 12 or above, from about 7 to 11, about 8-12, about 7-11, about 9-12, or about 10-12.

Beneficially, the methods of treatment do not negatively interfere with the compatibility of the systems or a portion of a processing system, and further do not negatively interfere with the $SO_2$ scrubbing process. In a beneficial aspect, the method of treatment does not result in any negative impact on performance of the system and/or the effluent from the system. As one skilled in the art will appreciate, effluent from a system will often be sent into a waste treatment facility (e.g. in grain facilities and/or paper making processes) and the treatment with the biocide compositions will result in any effluent having been treated to remove microbes and/or other contaminants within the system that would otherwise flow through the effluent into a waste treatment facility and adding additional burden onto such system. Furthermore, some of the methods of treatment do not require the stoppage of $SO_2$ scrubber's normal operation and reduce $SO_2$ leakage to environment. The methods of treatment certainly reduce or eliminate CIP cleanings that requires at least stoppage of blowers and a lot of bleach or other chemicals. The methods of treatment according to the invention provide broad antimicrobial efficacy. In a particular aspect, the methods of treatment according to the invention provide biofilm antimicrobial and biocidal efficacy. Exemplary microorganisms susceptible to the biocide compositions of the invention include, gram positive bacteria (e.g., *Staphylococcus aureus, Bacillus* species (sp.) like *Bacillus subtilis*, Clostridia sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* and *Desulfotomaculum* species. The preferred microorganisms susceptible to the biocide compositions of the invention include anaerobic and aerobics or blends of microorganisms existing in $SO_2$ scrubbers.

In an aspect, the methods of treatment with the biocide compositions can further comprise additional treatment cycles selected from an acidic treatment, an alkaline treatment, an enzymatic treatment and/or a neutral treatment either before or after the biocide composition contacts the surface. Another step often used can be referred to as a pre-rinse step. In general, water and/or an alkaline solution can be run through the processing system to remove soils.

In some embodiments, the removing or preventing of microbial growth, biomass and/or mineral deposits from the scrubber surface prevents plugging and fouling, and enhances flow through the $SO_2$ scrubber. In some other embodiments, the surface is fouled with a biofilm and/or in need of biofilm remediation and/or prevention. In some other embodiments, the surface is also fouled with additional contaminants and/or impurities in need of remediation and/or prevention.

In some embodiments, the method further comprises a first step of generating the biocide composition in situ and/or in-line and/or combining one or more biocides to provide the biocide composition. In some other embodiments, the method further comprises a pre-rinse or flushing step of washing the surface with water and/or an alkaline and/or acidic solution.

In some other embodiments, the method further comprises additional treatment cycles comprising an acidic treatment, an enzymatic treatment, an alkaline treatment and/or a neutral treatment either before or after the biocide composition contacts the surface. In some other embodiments, the methods do not include any additional treatment cycles comprising an acidic treatment, an enzymatic treatment, an alkaline treatment and/or a neutral treatment either before or after the biocide composition contacts the surface.

In some embodiments, the surface is contacted continuously with the biocide composition during its normal operation. In some embodiments, the one or more biocides are dosed continuously into the biocide composition. In preferred embodiments, the one or more biocides are dosed continuously during the normal operation of the $SO_2$ scrubber. In an aspect, the continuous or constant dosing can be provided into a sump of the system, such that the biocide composition is circulated through the system, including for example recirculating loops, to contact hard surfaces therein.

In other embodiments, the one or more biocides are dosed non-continuously, in pulse, or in a time interval. In some embodiments, during a pulse dosing (also conventionally referred to as intermittent or slug dosing), the one or more biocides are dosed for at least 60 seconds, at least 2 minutes, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, or at least 60 minutes. In some other embodiments, the one or more biocides are dosed at least about every week, or at least about every other day, or at least about every day, or at least about every 12 hours, or at least about from every 4 to about every 6 hours. In some embodiments, the surface is being contacted by biocide composition and no other active chemistry(ies) are dosed to the system. In some other embodiments, the surface is contacted with the biocide composition at an ambient temperature or at the scrubber's normal operating temperature.

In some embodiments, wherein the surface is contacted with the biocide composition at a temperature from about 2° C. to 60° C. In some other embodiments, the temperature of the surface in need of treatment may be between about 2° C. to 60° C., between about 15° C. to 50° C., between about 18° C. to 40° C., or any range of there between. In some embodiments, the temperature of the surface treatment may be ambient temperatures, such as from 20° C. to 30° C.

In some embodiments, wherein the surface is an inside surface of any components that touch gases and liquids that are used for the scrubber's operation.

In some embodiments, the biocide composition removes about 100% of the microbial growth and biomass on a surface. In some embodiments, the biocide composition removes at least 95%, at least 90%, at least 80%, at least 70%, at least 60%, at least 50%, at least 40%, at least 30%, at least 20%, or at least 10% of the microbial growth, biomass and/or mineral deposit caused by a microorganism from the surface. In some embodiments, the biocide composition prevents or reduces the microbial growth, biomass and/or mineral deposit caused by a microorganism by at least 95%, at least 90%, at least 80%, at least 70%, at least 60%, at least 50%, at least 40%, at least 30%, at least 20%, or at least 10% on the surface. In some embodiments, the application of the biocide composition maintain at least 95%, at least 90%, at least 80%, at least 70%, at least 60%, at least 50%, at least 40%, at least 30%, at least 20%, or at least 10% of the air flow through the system, including the $SO_2$ scrubber, without increasing the pressure.

In a further beneficial aspect, the methods of cleaning using the biocide compositions and the percentage removal of microbial growth and biomass on a surface, along with the maintained air flow through the system without increasing the pressure, provides efficacious cleaning that complies with allowable emissions by increasing power to the pump. Within the $SO_2$ scrubbers, the delta pressure to maintain air flow through the system, including a system having a tower, can approach capacity of a pump. To reduce (or maintain) the pressure within the system that impacts air flow, convention methods have included replacement of packing materials within the scrubber (such as shown within The FIGURE). However, such solution is expensive and requires shut down of the system. Beneficially, the methods described herein of cleaning using the biocide compositions provide an alternative solution.

In some embodiments, the microorganism is an anaerobic or aerobic and the blend of microorganism typically existing in an $SO_2$ scrubber.

Additional Functional Ingredients

The components of the biocide compositions can further be combined with various functional components suitable for use in hard surface treatment. In some embodiments, the biocide compositions make up a large amount, or even substantially all of the treatment composition for the scrubber as disclosed herein except water. For example, in some embodiments few or no additional functional ingredients are disposed therein. In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

In some embodiments, the biocide compositions may include surfactants, such as for example nonionic and anionic surfactants, defoaming agents, anti-redeposition agents, solubility modifiers, dispersants, rinse aids, metal protecting agents, stabilizing agents, corrosion inhibitors, sequestrants and/or chelating agents, wetting agents, water conditioning agents or chelants, enzymes, rheology modifiers or thickeners, hydrotropes or couplers, buffers, solvents and the like.

Water

The biocide compositions according to the invention may comprise water in amounts that vary depending upon techniques for processing the composition. Water provides a medium which dissolves, suspends, or carries the other components of the composition. Water can also function to deliver and wet the composition of the invention on an object. In some embodiments, water makes up a large portion of the composition of the invention and may be the balance of the composition. The water amount and type will depend upon the nature of the composition as a whole, the environmental storage, and method of application including concentration composition, form of the composition, and intended method of delivery, among other factors. Notably the carrier should be chosen and used at a concentration which does not inhibit the efficacy of the functional components in the composition of the invention for the intended use.

Builders

The present compositions can include a builder. Builders include chelating agents (chelators), sequestering agents (sequestrants), and the like. The builder may act to stabilize the cleaning composition or use solution. Examples of builders include, but are not limited to, phosphonates, phosphates, aminocarboxylates and their derivatives, pyrophosphates, polyphosphates, ethylenediamene and ethylenetriamene derivatives, hydroxyacids, and mono-, di-, and tri-carboxylates and their corresponding acids. Other exemplary builders include aluminosilicates, nitroloacetates and their derivatives, and mixtures thereof. Still other exemplary builders include aminocarboxylates, including salts of ethylenediaminetetraacetic acid (EDTA), hydroxyethylenediaminetetraacetic acid (HEDTA), and diethylenetriaminepentaacetic acid. For a further discussion of chelating agents/sequestrants, see Kirk-Othmer, Encyclopedia of Chemical Technology, Third Edition, volume 5, pages 339-366 and volume 23, pages 319-320, which is incorporated in its entirety. According to an aspect of the invention, preferred builders are water soluble, biodegradable and phosphorus-free. The amount of builder in the cleaning composition or use solution, if present, is typically between about 10 ppm and about 1000 ppm in the cleaning composition or use solution.

Acidulants, Catalysts and Enzymes

Acidulants may be included as additional functional ingredients in a composition according to the invention. In an aspect, a strong mineral acid such as nitric acid, sulfuric acid, phosphoric acid or a stronger organic acid such as methyl sulfonic acid (MSA) can be used. In addition, some strong mineral and organic acids, such as nitric acid, provide a further benefit of reducing the risk of corrosion. In some embodiments, the present composition does not comprise a mineral acid or a strong mineral acid.

Acidulants, catalysts and/or enzymes may be employed in amounts sufficient in a use solution in an amount of at least about 0.1 wt-% to about 10 wt-%, preferably at least about 0.1 wt-% to about 5 wt-%, more preferably from about 0.1 wt-% to about 1 wt-%.

Surfactants

The surfactants described hereinabove can be used singly or in combination with the methods of the present invention. In particular, the nonionics and anionics can be used in combination. The semi-polar nonionic, cationic, amphoteric and zwitterionic surfactants can be employed in combination with nonionics or anionics. The above examples are merely specific illustrations of the numerous surfactants which can find application within the scope of this invention. It should be understood that the selection of particular surfactants or combinations of surfactants can be based on a number of factors including compatibility with the membrane at the intended use concentration and the intended environmental conditions including temperature and pH. Accordingly, one should understand that surfactants that may damage a particular membrane during conditions of use should not be used with that membrane. It is expected that the same surfactant, however, may be useful with other types of membranes. In addition, the level and degree of foaming under the conditions of use and in subsequent recovery of the composition can be a factor for selecting particular surfactants and mixtures of surfactants. For example, in certain applications it may be desirable to minimize foaming and, as a result, one would select a surfactant or mixture of surfactants that provides reduced foaming. In addition, it may be desirable to select a surfactant or a mixture of surfactants that exhibits a foam that breaks down relatively quickly so that the composition can be recovered and reused with an acceptable amount of down time. In addition, the surfactant or mixture of surfactants can be selected depending upon the particular soil that is to be removed.

It should be understood that the compositions for use with the methods of the present invention need not include a surfactant or a surfactant mixture, and can include other components. In addition, the compositions can include a surfactant or surfactant mixture in combination with other components. Exemplary additional components that can be provided within the compositions include builders, water conditioning agents, non-aqueous components, adjuvants, carriers, processing aids, enzymes, and pH adjusting agents. When surfactants are included in the peroxyformic acid compositions in a use solution they can be included in an amount of at least about 0.1 wt. % to about 10 wt. %.

Anionic Surfactants

The biocide compositions can contain a surfactant component(s) that includes a detersive amount of an anionic surfactant or a mixture of anionic surfactants. Anionic surfactants are desirable in cleaning compositions because of their wetting, detersive properties, and often times good compatibility with membranes. The anionic surfactants that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates. Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate. Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium C14-C17 secondary alkyl sulfonate. Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms. Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether ethoxylate sulfate. Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate. Suitable alcohol sulfates that can be used in the cleaning composition include those having an alcohol group containing about 6 to about 24 carbon atoms.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678. The disclosures of the above references relating to anionic surfactants are incorporated herein by reference.

Nonionic Surfactants

The biocide compositions can contain a surfactant component(s) that includes a detersive amount of a nonionic surfactant or a mixture of nonionic surfactants. Nonionic surfactants can be included in the composition to enhance soil removal properties. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties.

Nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt. %.

Additional nonionic surfactants include alcohol alkoxylates. A suitable alcohol alkoxylate include linear alcohol ethoxylates. Additional alcohol alkoxylates include alkylphenol ethoxylates, branched alcohol ethoxylates, secondary alcohol ethoxylates, castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauramide diethanolamide, cocoamide diethanolamide, polyethylene glycol cocoamide, oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl glucosides, or mixtures thereof.

Other exemplary nonionic surfactants for use with the methods of the present invention are disclosed in the treatise Nonionic Surfactants, edited by Schick, M. J., Vol. 1 of the Surfactant Science Series, Marcel Dekker, Inc., New York, 1983, the contents of which is incorporated by reference herein. A typical listing of nonionic classes, and species of these surfactants, is also given in U.S. Pat. No. 3,929,678. Further examples are given in "Surface Active Agents and Detergents" (Vol. I and II by Schwartz, Perry and Berch). The disclosures of these references relating to nonionic surfactants are incorporated herein by reference.

Amphoteric Surfactants

Amphoteric surfactants can also be used to provide desired detersive properties. Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Zwitterionic Surfactants

In some embodiments, zwitterionic surfactants are used with the methods of the invention. Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A typical listing of zwitterionic classes, and species of these surfactants, is given in U.S. Pat. No. 3,929,678. Further examples are given in "Surface Active Agents and Detergents" (Vol. I and II by Schwartz, Perry and Berch). The disclosures of zwitterionic surfactants in the above references are incorporated herein by reference.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A few exemplary biocides or a combination of one or more quaternary ammonium compounds with one additional biocide were investigated for their ability to inhibit microorganism growth. The results are listed in Table 1. The method used to generate the data in Table 1 was based on methods for identifying the minimum inhibitory concentration of biocides or biocidal agents for use in anaerobically contaminated aqueous system as disclosed in the patent publication WO9934013A1 by Schwingel, et. al.

The method was a test assay used to rapidly screen antimicrobial agents against bacterial populations native to the test sample under anaerobic conditions. The assay utilized a pH indicator dye which is red at pH levels above 6.5 and yellow below pH 6.5. During fermentation under anaerobic conditions, volatile fatty acids were produced, which lowered the pH of the system. In the test wells, the accumulation of volatile fatty acids from actively growing and fermenting microorganisms lowered the pH causing the indicator dye to turn yellow. When biocides were present and effective in inhibiting or killing the microorganisms in the test wells, no color change was observed and the test wells remained red.

Water samples required rough filtration to remove particulates that interfere with pipetting and liquid transfer. The pH of the sample was adjusted to 6.5 with dilute NaOH or HCl. The pH adjustment was critical since the indicator dye is based on a pH change. Nutrient solution and the indicator dye were added to the sample. The resulting solution was dosed with biocides and serially diluted to achieve the desired test concentrations. Treated and untreated water samples were then incubated under anaerobic conditions.

When the control sample had turned yellow due to active fermentation and acid production, all samples were examined for color change, and the Minimum Inhibitory Concentration (MIC) values recorded. This process took from between 6 hours to 24 hours depending on the microbial population present in the wells being tested. Because MIC values change with extended contact time, it was important to read the MIC values within 2-3 hours of the control wells turning yellow. Samples can also be plated to determine the biocidal effect of the treatments.

TABLE 1

Minimum Inhibitory Concentration (ppm product)

| Biocide Product | Minimum Inhibitory Concentration (ppm) |
| --- | --- |
| 3,5-dimethyl-tetrahydro-2H-1,3,5-thiadiazine-2-thione | 26.25 |
| Methylenebisthiocyanate | 0.8-1.6 |
| sodium dimethyldithiocarbamate, disodium ethylene bis-dithiocarbamate | 18.9-37.5 |
| bis-(trichloromethyl)-sulfone, methyl n-$C_{14}$-$C_{18}$-dialkyl ammonium chloride, n-$C_{14}$-$C_{18}$-alkyl dimethyl benzyl ammonium chloride | 2.68 |
| Glutaraldehyde, dimethyl tetradecyl ammonium chloride | 4-8 |

While this invention may be embodied in many different forms, there are described scientific papers, and any other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

What is claimed is:

1. A method for removing and/or reducing microbial growth and biofilm on a hard surface inside an $SO_2$ scrubber system comprising:
   dosing a biocide composition comprising from about 0.1 ppm to about 150 ppm of one or more biocides into a sump or recirculation sump within an $SO_2$ scrubber system and/or into the water feed line of the $SO_2$ scrubber system;
   contacting a hard surface comprising packing materials inside the $SO_2$ scrubber system with the biocide composition,
   wherein the one or more biocides comprise 3,5-dimethyl-tetrahydro-2H-1,3,5-thiadiazine-2-thione, sodium dimethyldithiocarbamate, disodium ethylene bis-dithiocarbamate, bis-(trichloromethyl)-sulfone, glutaraldehyde, or combinations thereof;
   wherein the method does not require stopping of the normal operation of the $SO_2$ scrubber system;
   wherein the microbial growth and biofilm comprises both aerobic microorganisms and anaerobic microorganisms; and
   wherein the surface is contacted with the biocide composition at a temperature of between about 2° C. to about 60° C.

2. The method of claim 1, wherein the biocide composition is a liquid solution used in the normal operation of the $SO_2$ scrubber, and wherein the hard surface is in continuous contact with the biocide composition.

3. The method of claim 1, wherein the one or more biocides further comprise a quaternary ammonium compound.

4. The method of claim 3, wherein the biocide composition comprises from about 1 ppm to about 50 ppm of: the quaternary ammonium compound and the glutaraldehyde; the quaternary ammonium compound and the bis-(trichloromethyl)-sulfone; the quaternary ammonium compound, the disodium ethylene bis-dithiocarbamate, and the sodium dimethyldithiocarbamate; the quaternary ammonium compound and 3,5-dimethyl-tetrahydro-2H-1,3,5-thiadiazine-2-thione; the quaternary ammonium compound, the one or more biocides and further comprising a sulfone; the quaternary ammonium compound, the one or more biocides and further comprising one or more dithiocarbamates; the quaternary ammonium compound, the one or more biocides and further comprising a thiocyanate derivative; the quaternary ammonium compound, the one or more biocides and further comprising a tetrahydro-2H-1,3,5-thiadiazine-2-thione derivative; or the quaternary ammonium compound, the one or more biocides and further comprising a methylenebis-thiocyanate.

5. The method of claim 1, wherein the biocide composition comprises from about 0.1 ppm to about 100 ppm of the one or more biocides.

6. The method of claim 1, wherein the reducing of microbial growth and biofilm from the scrubber surface reduces plugging and fouling, and enhances flow through the $SO_2$ scrubber.

7. The method of claim 1, wherein the surface is also fouled with additional contaminants and/or impurities in need of remediation and/or reduction.

8. The method of claim 1, further comprising a first step of generating the biocide composition in situ and/or in-line and/or combining one or more biocides to provide the biocide composition.

9. The method of claim 1, further comprising a pre-rinse or flushing step of washing the surface with water and/or an alkaline and/or acidic solution.

10. The method of claim 1, further comprising an additional treatment cycle, wherein the treatment cycle is an acidic treatment, an enzymatic treatment, an alkaline treatment and/or a neutral treatment either before or after the biocide composition contacts the surface.

11. The method of claim 1, wherein the method does not include an acidic treatment, an enzymatic treatment, an alkaline treatment and/or a neutral treatment either before or after the biocide composition contacts the surface.

12. The method of claim 1, wherein the biocide composition is dosed continuously into the $SO_2$ scrubber.

13. The method of claim 1, wherein the biocide composition is dosed non-continuously or in a pulse fashion into the $SO_2$ scrubber.

14. The method of claim 13, wherein the biocide composition is dosed at least weekly, or at least about every other day, or at least about every day, or at least about every 12 hours, or at least about from every 4 to about every 6 hours.

15. The method of claim 1, wherein when the surface is contacted by the biocide composition, the biocide composition is the only active chemistry dosed into the system for removing and/or reducing microbial growth and biofilm.

16. The method of claim 1, wherein the hard surface is contacted with the biocide composition at a temperature from about 15° C. to about 50° C.

17. The method of claim 1, wherein the application of the biocide composition maintains at least about 90% of the air flow within the $SO_2$ scrubber without increasing the pressure within the system.

18. The method of claim 1, wherein the biofilm further comprises fungi, mold, algae, protozoa, archaea, or a combination thereof.

19. A method for removing and/or reducing microbial growth and biofilm on a hard surface inside an $SO_2$ scrubber system comprising:
   dosing a biocide composition comprising from about 0.1 ppm to about 150 ppm of one or more biocides into a sump or recirculation sump within an $SO_2$ scrubber system and/or into the water feed line of the $SO_2$ scrubber system;
   contacting a hard surface comprising packing materials inside the $SO_2$ scrubber system with the biocide composition,
   wherein the one or more biocides comprise a quaternary ammonium compound and at least one of 3,5-dimethyl-tetrahydro-2H-1,3,5-thiadiazine-2-thione, sodium dimethyldithiocarbamate, disodium ethylene bis-dithiocarbamate, bis-(trichloromethyl)-sulfone, glutaraldehyde, or combinations thereof;

wherein the method does not require stopping of the normal operation of the $SO_2$ scrubber system;

wherein the microbial growth and biofilm comprises both aerobic microorganisms and anaerobic microorganisms; and wherein the surface is contacted with the biocide composition at a temperature of between about 2° C. to about 60° C.

20. The method of claim 19, wherein the biocide composition comprises from about 1 ppm to about 150 ppm of: the quaternary ammonium compound and the glutaraldehyde; the quaternary ammonium compound and the bis-(trichloromethyl)-sulfone; the quaternary ammonium compound, the disodium ethylene bis-dithiocarbamate, and the sodium dimethydithiocarbamate; the quaternary ammonium compound and 3,5-dimethyl-tetrahydro-2H-1,3,5-thiadiazine-2-thione; the quaternary ammonium compound, the one or more biocides and further comprising a sulfone; the quaternary ammonium compound, the one or more biocides and further comprising one or more dithiocarbamates; the quaternary ammonium compound, the one or more biocides and further comprising a thiocyanate derivative; the quaternary ammonium compound, the one or more biocides and further comprising a tetrahydro-2H-1,3,5-thiadiazine-2-thione derivative; or the quaternary ammonium compound, the one or more biocides and further comprising a methylenebisthiocyanate.

* * * * *

UNITED STATES PATENT AND TRADEMARK OFFICE
CERTIFICATE OF CORRECTION

| | | |
|---|---|---|
| PATENT NO. | : 11,071,301 B2 | Page 1 of 1 |
| APPLICATION NO. | : 15/783169 | |
| DATED | : July 27, 2021 | |
| INVENTOR(S) | : Junzhong Li, Chris Nagel and Laura Rice | |

It is certified that error appears in the above-identified patent and that said Letters Patent is hereby corrected as shown below:

In the Claims

Column 31, Claim 20, Line 18:
DELETE "dimethydithiocarbamate;" after "sodium"
INSERT --dimethyldithiocarbamate;-- after "sodium"

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*